United States Patent
Wang et al.

(10) Patent No.: US 6,894,169 B1
(45) Date of Patent: May 17, 2005

(54) ZWITTERIONIC CHROMOPHORES AND POLYMERS CONTAINING SUCH CHROMOPHORES

(75) Inventors: Zhi Yuan Wang, Ottawa (CA); Naiheng Song, Ottawa (CA); Andrew Beaudin, Ottawa (CA); Cara Weir, Ottawa (CA); Graham Cross, Bishopton (GB); Marek Szablewski, Durham (GB)

(73) Assignee: Nortel Networks Limited, St. Laurent (CA)

( * ) Notice: Subject to any disclaimer, the term of this patent is extended or adjusted under 35 U.S.C. 154(b) by 70 days.

(21) Appl. No.: 10/227,846

(22) Filed: Aug. 27, 2002

(51) Int. Cl.$^7$ ............... C07D 211/70; C09K 19/30; C08F 18/00
(52) U.S. Cl. ............ 546/330; 252/299.63; 526/292.2
(58) Field of Search ............... 546/330; 252/299.63; 526/292.2

(56) References Cited

U.S. PATENT DOCUMENTS 5,869,693 A    2/1999  Wang
6,610,809 B1 * 8/2003  Yamamoto et al. ...... 526/292.2

FOREIGN PATENT DOCUMENTS

CA         A-2346149       5/2001

OTHER PUBLICATIONS

Abrahart, Dyes and their Intermediates, Pergamon press, (1968), pp. 8.*
Dalton, L.R., et al. *Opt. Lett,* 1998, 23, 478.
Szablewski, M.; Bloor, D.; Cross, G.H., et al. *J. Am. Chem. Soc.* 1997, 119, 3144.
Metzger, R. M.; Heimer, N. E.; Ashwell, G. J. *Mol. Cryst. Liq. Cryst.* 1984, 107, 133.
Ashwell, G. J.; Dawnay, E. J. C.; Kuczynski, A. P.; Szablewski, M.; Sandy, I. M.; Bryce, M. R.; Grainger, A. M.; Hasan, M. *J. Chem. Soc., Faraday Trans.* 1990, 86(7), 1117.
Ashwell, G. J.; Malhotra, M.; Bryce, M. R.; Grainger, A. M. *Synth. Met.* 1991, 43, 3173.
Bell, N. A.; Broughton, R. A.; Brooks, J. S.; Jones, T. A.; Thorpe, S. C.; Ashwell, G. J. *J. Chem. Soc., Chem. Commun,* 1990, 325.

* cited by examiner

*Primary Examiner*—Cecilia J. Tsang
*Assistant Examiner*—Raymond Covington
(74) *Attorney, Agent, or Firm*—Blake, Cassels & Graydon LLP; George E. Fisk

(57) ABSTRACT

A non-linear chromophore is obtained by reacting a picolinium halide having a desired functional group (preferably —OH) with a lithium TCNQ adduct. If desired, the chromophore can be graft polymerized onto a polymer which has complementary functional groups (preferably carboxyl groups). Optionally the polymer can then be cross-linked. Such polymers are useable in electro-optical devices.

20 Claims, No Drawings

ZWITTERIONIC CHROMOPHORES AND POLYMERS CONTAINING SUCH CHROMOPHORES

This invention relates to zwitterionic nonlinear optical materials, and graft polymers having such materials attached as side groups.

BACKGROUND OF THE INVENTION

An important component for dense wavelength division multiplexing (DWDM) systems is a high-speed, low-voltage modulator, which is usually called an "electro-optic modulator" or "electro-optic device". It is also known as an EO modulator or EO device. The materials suitable for use in such a modulator should have the nonlinear optical (NLO) property with large electro-optic coefficients (e.g., >50 pm/V) at the desired telecommunication wavelengths. Telecommunication wavelengths are those prescribed by some standard setting body such as the International Telecommunications Union (ITU). Common telecommunication systems use, for example, 1310 nm and bands of 1485–1525 nm, 1525–1562 nm and 1565–1620 nm, as prescribed by the ITU.

The electric polarization of a medium subjected to external electric fields can be written as:

$$P_i(\omega)=P_i^0+\chi_{ij}^{(1)}(-\omega)E_j(\omega)+\chi_{ijk}^{(2)}(-\omega,\omega_1,\omega_2)E_j(\omega_j(\omega_1)$$

$$E_k(\omega_2)+$$

$$\chi_{ijkl}^{(3)}(-\omega,\omega_1,\omega_2,\omega_3)E_j(\omega_1)E_k(\omega_2)E_l(\omega_3)+ \ldots$$

where $P_i^0$ is the static polarization and the rest terms are the linear $[\chi_{ij}^{(1)}]$ and nonlinear $[\chi_{ijk}^{(2)}, \chi_{ijkl}^{(3)}, \ldots]$ susceptibility tensors. The second-order nonlinearity includes second harmonic generation $[\chi_{ijk}(-\omega,\omega_1,\omega_2)]$ and the linear EO effect (Pockels effect) $[\chi_{ijk}^{(2)}(-\omega,0,\omega_2)]$. The Pockels effect is the effect of interest for EO modulator device application. It is related to the equivalent molecular hyperpolarizability β. A strong asymmetric 'push-pull' molecule with both electron accepting and electron donating groups linked by a conjugated moiety usually shows a finite β value.

The EO effect is not a naturally occurring property in polymers, in contrast to the situation in crystal materials such as lithium niobate. Instead, in polymers it is the product of custom synthesis and an alignment (poling) procedure. The poling process is facilitated by a high ground state dipole moment of an NLO polymer. The induced linear EO coefficient parallel to an applied field is given by:

$$\chi_{zzz}^{(2)}=N\beta_{111}f_\omega^2 f_0^2 \mu E/5kT$$

where N is the density of NLO chromophore, $\beta_{111}$ is the first hyperpolarizability of the chromophore in the direction of $\mu$, $f_{107}^{\ 2}$ and $f_0^2$ are local field correction factors at frequencies $\omega$ and zero respectively, $\mu$ is the ground state dipole moment of the chromophore, E is the applied electric field and T is the temperature.

The fact that the dielectric constant of polymers is typically one order of magnitude lower than that in lithium niobate indicates that NLO polymers would be suited to the EO modulator application. Polymers could in principle exceed the performance of current ferroelectric materials for high-frequency EO devices. Additional polymer properties which favor the use of organic polymers in the photonic device applications are their ease and versatility of processing and integrability and synthetic versatility.

To obtain useful properties for an EO polymer, it is desirable to maximize N and the product $\mu\beta$. The former is determined by the number of active NLO chromophores in the polymer and the latter is a property of the chromophore utilized. Another important requirement is to have a functional group that allows the chromophore to be incorporated into or grafted onto a host polymer. Incorporation or grafting of chromophore into a host polymer is a necessary step towards the device fabrication, as the host polymer material provides a framework that can be processed into a waveguide structure.

A large number of chromophores without functional groups for grafting have been synthesized and some of these exhibit very large macroscopic nonlinearities in guest/host poled polymers. Two NLO chromophores, chromophore-1 reported by Dalton et al (*Opt. Lett,* 1998, 23, 478) and DEMI reported by Szablewski et al (*J. Am. Chem. Soc.* 1997, 119, 3144) have the following structures:

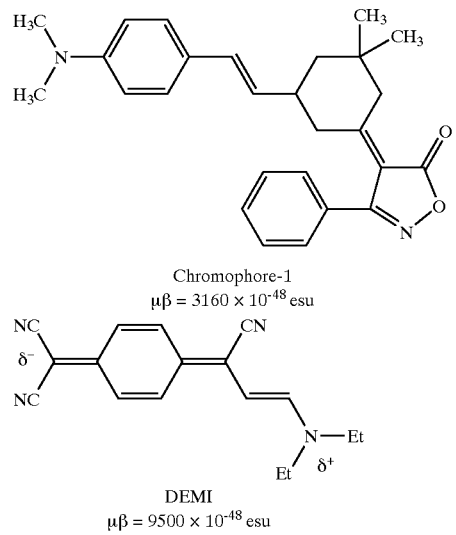

Chromophore-1
$\mu\beta = 3160 \times 10^{-48}$ esu

DEMI
$\mu\beta = 9500 \times 10^{-48}$ esu

A series of zwitterionic chromophores structurally similar to DEMI but containing the pyridinium and quinolinium moieties has been reported. (Metzger et al, *Mol. Cryst. Liq. Cryst.* 1984, 107, 133; Ashwell et al *J. Chem. Soc., Faraday Trans.* 1990, 86(7), 1117.; and *Synth. Met.* 1991, 43, 3173: Bell et al *J. Chem. Soc., Chem. Commun,* 1990, 325.) These chromophores have the formulae:

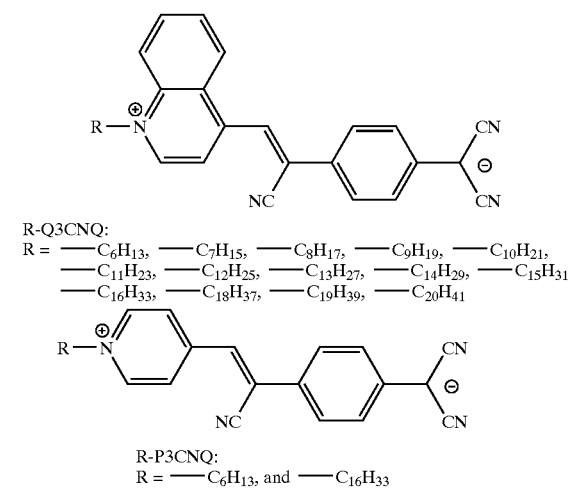

R-Q3CNQ:
R = —$C_6H_{13}$, —$C_7H_{15}$, —$C_8H_{17}$, —$C_9H_{19}$, —$C_{10}H_{21}$,
—$C_{11}H_{23}$, —$C_{12}H_{25}$, —$C_{13}H_{27}$, —$C_{14}H_{29}$, —$C_{15}H_{31}$
—$C_{16}H_{33}$, —$C_{18}H_{37}$, —$C_{19}H_{39}$, —$C_{20}H_{41}$

R-P3CNQ:
R = —$C_6H_{13}$, and —$C_{16}H_{33}$

None of these chromophores has a functional group which permits covalent bonding. Therefore, these chromophores can not be linked to a host polymer via covalent bonding and thus have no practical value for use in an electro-optical device such as electro-optical modulator.

DESCRIPTION OF THE INVENTION

The present invention provides generally a new type of nonlinear optical chromophore that contains a functional group which permits it to be grafted onto a host polymer, and a method of making such a chromophore. The invention further provides generally a new type of nonlinear optical polymer containing a high content of the said chromophore and showing a good solubility in organic solvents and good film-forming ability.

According to the invention, a picolinium halide is prepared by reacting the halide of an organic compound having a desired functional group with 4-picoline. This produces a picolinium halide having the desired functional group. It has the general formula I, as follows:

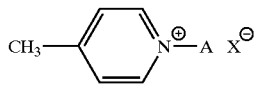

where A is a linear or branched alkyl group having up to 20 carbon atoms and the desired functional group, and X is —Cl, —Br or —I, and is preferably —Br. Preferably, the desired functional group is —OH. The linear or branched alkyl group can have fluorine substituents if desired. Preferred alkyl groups have from 2 to 6 carbon atoms.

The picolinium halide is then reacted with a lithium-tetracyanoquinodimethine) adduct (usually called a lithium-TCNQ adduct) to form a picoliniumquinodimethine ((PQDM) chromophore according to the invention. This has the general formula II, as follows:

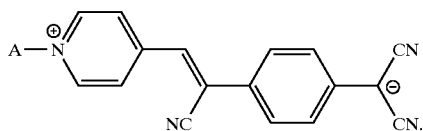

where A has at least one desired functional group connected to a linear or branched $C_2$–$C_{20}$ alkyl groups and the alkyl group can have fluorine substituents. The desired functional group is preferably hydroxyl. Preferably A has at least one hydroxyl group connected to a linear or branched $C_2$–$C_6$ alkyl group.

The PQDM chromophore retains the desired functional group that was in the picolinium halide. Preferably, this group is hydroxyl.

The invention also includes polymers having side chains with the inventive chromophores. The host polymer can be any polymer which has good solubility in at least one organic solvent and which is film forming from such solvent, and which has complementary functional groups to those of the chromophore. Preferably, it should also have a relatively high glass transition temperature, so that waveguides and the like made from it are heat-resistant.

The chromophores are grafted onto the host polymer by reacting their functional groups with the complementary functional groups of the host polymer.

A preferred polymer is a polyimide (polyimide III, the formula of which is given below) prepared from 3,5-diaminobenzoic acid (DABA) and hexafluoroisopropylidene-2,2-bisphthallic anhydride (6FDA) {. The reaction is as follows:

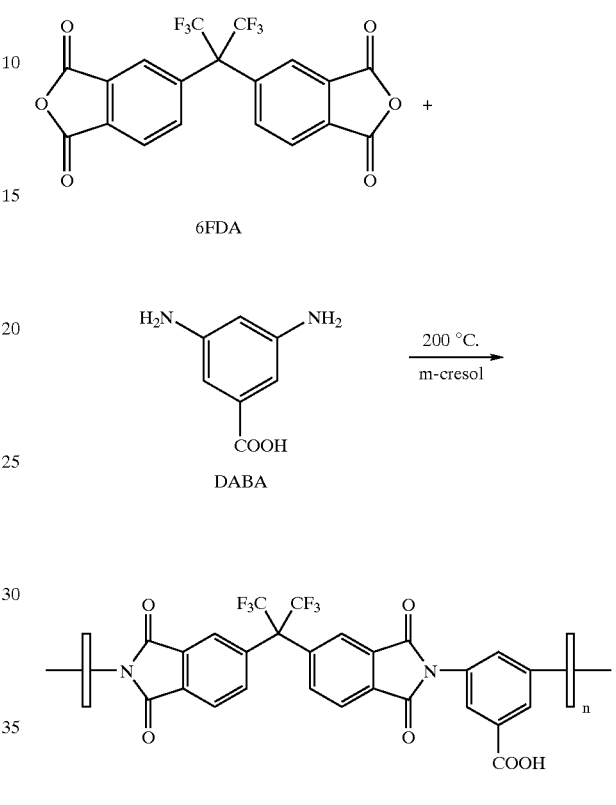

Scheme 1. Synthesis of the Acid-Containing Host Polyimide III

The polymer III is soluble in a number of common organic solvents, and can be cast as a film from such solvents. It shows no glass transition temperature up to 450° C. by differential scanning calorimetry.

It is preferred that the desired functional group be a hydroxyl group, as the reactions proceed without undue side reactions which affect the hydroxyl group. However, other functional groups can be used, provided they can be suitably protected, if necessary, during the reaction to form the picolinium halide and suitably de-protected without damaging their chromophore properties at a subsequent time before grafting onto a polymer.

The chromophore II is grafted onto the host polymer to give a graft polymer IV with chromophore groups. Optionally, as described below, the host polymer can have additional groups grafted onto it, as blocking or crosslinking groups. The polymer has the general formula:

IV

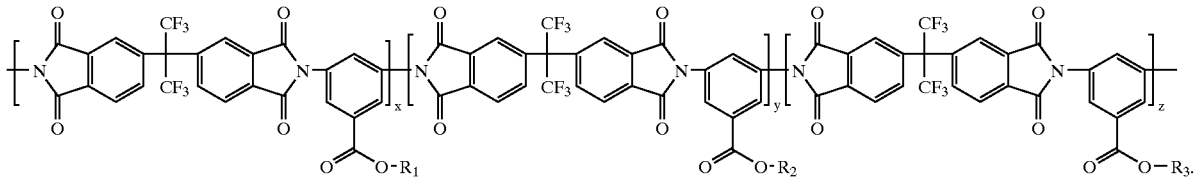

Where $R_1$ is a chromophore moiety which remains when a chromophore II is reacted with polymer III,
$R_2$ is a blocking moiety which remains when a bulky alcohol is reacted with polymer III
$R_3$ is a crosslinking moiety which remains when a compound containing a crosslinking group and a hydroxyl is reacted with polymer III, and wherein
x is at least 1%, and x+y+z=100%, and either or both of y and z can be zero.

DETAILED DESCRIPTION OF THE INVENTION

The invention will be further described with reference to the following examples, which are intended to be illustrative of the invention but not limitative.

A. Preparation of Picolinium Salts.

The following picolinium salts (designated herein as compounds Ia–Ie) were prepared.

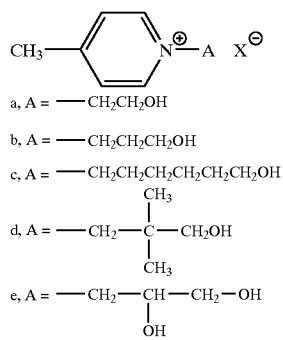

The structure and purity of the picolinium salts Ia–e were demonstrated and checked by IR and NMR spectrometry.

EXAMPLE 1
N-(3-hydroxypropyl)-4-picolinium bromide (Ib)

Anhydrous ethanol (250 mL) was added to a two-neck, 1 L round-bottomed flask, flushed with nitrogen, followed by addition of 3-bromo-1-propanol (60.0 g, 0.4317 mol) and 4-picoline (43.8 g, 0.4701 mol). The mixture was heated with stirring at 60° C. for 24 hours under nitrogen. The reaction was stopped and the contents in flask were transferred to a one-neck round-bottomed flask. The solvent was removed under vacuum leaving the product as a viscous, dark yellow-orange liquid. The product was washed within the same flask with diethyl ether (4×100 mL) and any remaining solvent was removed under vacuum. The yield of N-(3-hydroxypropyl)-4-picolinium bromide was 96.6 g (96% yield). $^1$H NMR (400 MHz, DMSO-d$_6$): δ 8.98 (2H, d, J=6.8 Hz), 8.00 (2H, d, J=6.8 Hz), 4.64 (2H, t, J=7.0 Hz, 7.0 Hz), 3.44 (2H, t, J=6.0 Hz, 6.0 Hz), 2.62 (3H, s), 2.06 (2H, p, J=6.8 Hz, 6.0 Hz, 6.0 Hz, 6.8 Hz). IR (neat): 3332 cm$^{-1}$ (O—H), 1642 cm$^{-1}$ (>C=N—C), 1518 cm$^{-1}$ (C—C aromatic).

EXAMPLE 2
N-(2-hydroxyethyl)-4-picolinium bromide (Ia)

In a 3-neck, round-bottomed flask flushed with nitrogen, 2-bromo-1-ethanol (40.01 mmol), 4-picoline (43.57 mmol) and absolute ethanol (16 mL) were combined and heated for 3.5 hours at 50° C. under nitrogen with stirring. The reaction was stopped and the contents of the flask were transferred to a one-neck round-bottomed flask. The solvent was removed under vacuum and the residue was washed with diethyl ether (4×100 ml) and any remaining solvent was removed under vacuum. The product was obtained as a viscous orange liquid in a 34% yield. $^1$H NMR (200 MHz, CDCl$_3$) 8.9 (2H, protons on pyridine ring), 8.0 (2H, protons on pyridine ring), 2.6 (3H, CH$_3$), 4.6 (2H, —CH$_2$O), 3.8 (2H, —NCH$_2$—), 5.2 (1H, —OH); IR (neat, cm$^{-1}$) 3303 (OH), 1640 (aromatic C=N), 1474 (aromatic C—C).

EXAMPLE 3
N-(6-hydoxyhexyl)-4-picolinium bromide (Ic)

6-Bromo-1-hexanol (27.61 mmol), 4-picoline (30.07 mmol) and absolute ethanol (16 mL) were added to a 3-neck, round-bottomed flask, and were heated at reflux The reaction was stopped after 36 hours. The solvent was removed under vacuum and the residue was washed with diethyl ether (4×100 ml), after which any remaining solvent was removed by vacuum. The product was obtained as an orange-yellow viscous liquid in a 100% yield. $^1$H NMR (400 MHz, DMSO-d$_6$): δ 9.01 (2H, d, J=6.4 Hz), 8.02 (2H, d, J=6.4 Hz), 4.57 (2H, t, J=7.2 Hz, 7.2 Hz), 4.01 (1H, br), 3.37 (2H, t, J=6.4 Hz, 6.4 Hz), 2.26 (3H, s), 1.89 (2H, p, J=7.2 Hz, 7.2 Hz, 7.2 Hz), 1.21–1.49 (6H, m).

EXAMPLE 4
Picolinium Bromide Id

In a 3-neck, round-bottomed flask, a mixture of 4 picoline (1.56 g, 1.63 mmol), 3-bromo-2,2-dimethyl-1-propanol (2.47 g, 14.8 mmol), and anhydrous ethanol (16 mL) was stirred at reflux for 2 hours. The solvent was removed by rotavaporation, and the residue was washed with diethyl ether thoroughly to remove an excess of 4-picoline. The product was dried under vacuum at 60° C. and obtained as a viscous orange liquid (2.30 g, yield: 59%): $^1$H NMR (200 MHz, DMSO-d$_6$): δ 8.5 (2H, d), 7.3 (2H, d), 4.8 (3H, s), 3.5 (2H, d), 2.4 (2H, d), 1.0 (6H, m); IR (neat, cm$^{-1}$): 3286 ($υ_{O—H}$ of hydroxy group), 1612 ($v_{C—N}$ of picolinium unit).

EXAMPLE 5
1-(2,3-Dihydroxypropyl)-4-picolinium chloride (Ie)

A mixture of freshly distilled 4-picoline (10.0 g, 108 mmol) and 2,3-dihydroxy-1-chloropropane (10.0 g, 91 mmol) in a round-bottomed flask with no solvent present was heated at 80–100° C. in an oil bath for 72 h while protected from moisture by a calcium chloride drying tube. After cooling, a solid was formed and was broken up with the aid of a spatula, followed by addition of ethyl acetate (20 mL). The solid mass was collected by filtration and washed with ethyl acetate to give Ie as a moisture sensitive pale-brown solid (17.81 & 97%). Recrystallization from ethanol gave beige microcrystals, m.p. 157–158° C.; $^1$H NMR (200 MHz, DMSO-d$_6$) 8.88 (d, J=6.5 Hz, 2H), 7.97 (d, J=6.5 Hz, 2H), 5.66 (br s,1H, —CHOH, exchangeable in D$_2$O), 5.20 (br s, 1H, —CH$_2$OH, exchangeable in D$_2$O), 4.77 (dd, J=13.0, 3.1 Hz, 1H, —NCH$_2$), 4.47(dd, 3=13.0, 8.1 Hz, 1H, —NCH$_2$), 3.89(m, 1H, CHOH), 3.47–3.53 (n, 1H, lower field branch of AB quartet, —CH$_2$OH), 3.27–3.33 (m, 11, higher field branch of AB quartet, —CH$_2$OH), 2.60 (s, 3K, CH$_3$); $^{13}$C NMR (50 MHz, DMSO-d$_6$) 159.1 (CQ), 144.9 (CH), 128.1 (CH), 70.7 (CH), 63.0 (due to 2×CH$_2$), 21.7 (CH$_3$). The signal at 63.0 ppm is able to be resolved as two separate signals at 63.1 and 62.9 with D$_2$O as solvent.

B. Preparation of Functionalized PQDM Chromophores

A series of hydroxy-containing PQDM chromophores IIa–e were synthesized by reaction of lithium-TCNQ adduct (LiTCNQ) and the corresponding picolinium halide Ia–Ie in the presence of a base and at least one organic solvent. The general synthetic procedure is given for PMDQ chromophore fib (Example 6). Preferably, the reaction is carried out by first mixing LiTCNQ with the desired picolinium halide in boiling ethanol for 1 hour to 12 hours and then the ethanol solvent is replaced by a higher boiling solvent such as chlorobenzene, toluene and xylene. The reaction continued for another period of 12–96 hours. Alternatively, acetonitrile is chosen as the reaction solvent and the reaction is carried out up to 96 hours at the boiling temperature of the solvent, without change of solvent.

The base is an amine or nitrogen hetrocyclic. The preferred bases are pyridine, quinoline, 1,8-diazabicyclo[5,4,0] undec-7-ene (DBU), 1,4-diazabicyclo[2,2,2]octane (DABCO), N-methyl piperidine, and N-(2-hydroxyethyl)piperidine. Particularly preferred bases are DBU, DABCO and N-(2-hydroxyethyl)piperdine. It was noted that the choice of solvent and base had an effect on the purity and yield of the chromophore product. The solvents shown (ethanol, followed by chlorobenzene, toluene or xylene, or acetonitrile, with no change of solvent) are those preferred, although other organic solvents can be used if they give acceptable purity and yield. Similarly, the best purity and yield were found to occur with the particularly preferred bases, but other bases can be used.

The chromophores made were the following:

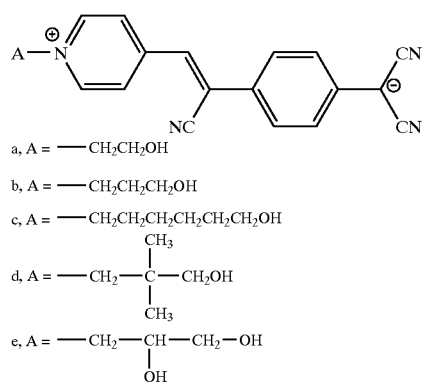

IIa-e

EXAMPLE 6
PQDM Chromophore IIb

To a solution of acetonitrile (100 mL) in a round-bottomed flask was added lithium-TCNQ adduct (LiTCNQ, 1.500 g, 7.100 mmol) and N-(3-hydroxypropyl)-4-picolinium bromide (Ib) (1.080 g, 7.100 mmol). While at reflux, 1.5 mL of N-(2-hydroxyethyl)piperidine was added and the resulting green solution was allowed to continue at reflux with monitoring by using an UV-Vis spectrophotometer. After 20 hours, the heating was stopped and the reaction vessel was allowed to cool to room temperature. The dark blue to black precipitate was filtered by suction and a small portion was recrystallized from acetonitrile to give a blue powder. Yield: 0.700 g (30%). $^1$H NMR (400 MHz, DMSO-d$_6$): δ 8.8 (d, 2H), 8.3 (d, 2H), 7.8 (s, 1H), 7.5 (d, 2H), 6.8 (d, 2H), 4.5 (t, 2H), 3.5 (t, 2H), 2.1 (m, 2H); UV-Vis: $\lambda_{max}$ 657 nm (N,N-dimethylformamide); IR (KBr, cm$^{-1}$): 3403 (O—H), 2174 and 2132 (CN), 1633 (C—C of picolinium moiety), 1565, 1547, 1505 (aromatic C—C).

EXAMPLE 7
PQDM Chromophore IIa

The procedure of Example 6 was followed, using picolinium salt Ia instead of Ib. A product having the following characteristics was obtained:
UV-Vis: $\lambda_{max}$ 657 nm (N,N-dimethylformamide); IR (KBr, cm$^{-1}$): 3403 (O—H), 2174 and 2132 (CN), 1633 (C—C of picolinium moiety), 1565, 1547, 1505 (aromatic C—C).

EXAMPLE 8
PQDM Chromophore IIc

The procedure of Example 6 was followed, using picolinium salt Ic instead of Ib. A product having the following characteristics was obtained:
UV-Vis: $\lambda_{max}$ 658 nm (N,N-dimethylformamide); IR (KBr, cm$^{-1}$): 3403 (O—H), 2174 and 2132 (CN), 1633 (C—C of picolinium moiety), 1565, 1547, 1505 (aromatic C—C).

EXAMPLE 9
PQDM Chromophore IId

The procedure of Example 6 was followed, using picolinium salt Id instead of Ib. A product having the following characteristics was obtained:
LV-Vis: $\lambda_{max}$ 657 nm (N,N-dimethylformamide); IR (KBr, cm$^{-1}$): 3403 (O—H), 2174 and 2132 (CN), 1633 (C—C of picolinium moiety), 1565, 1547, 1505 (aromatic C—C).

EXAMPLE 10
PQDM Chromophore IIe

The procedure of Example 6 was followed, using picolinium salt Ie instead of Ib and using piperidine instead of N-(2-hydroxyethyl)piperidine. A product having the following characteristics was obtained:
UV-Vis: $\lambda_{max}$ 657 nm (N,N-dimethylformamide) IR (KBr, cm$^{-1}$): 3403 (O—H), 2174 and 2132 (CN), 1633 (C—C of picolinium moiety), 1565, 1547, 1505 (aromatic C—C).

C—Preparation of Host Polymers

As the PQDM chromophores are functionalized with the hydroxy group, the host polymer needs to have another functional group that can be linked with the hydroxy group. These functional groups include, but not limited to, carboxylic acid, acid chloride, alkyl halide containing at least —CH$_2$X moiety where X=Cl, Br and I, isocyanato, epoxy and benzocyclobutenone. The carboxylic acid and benzocyclobutenone groups are the preferred functional groups to be used in the said host polymers, because the carboxylic acid is known to react with the hydroxy-containing compound to form the corresponding ester and because benzocyclobutenone is known to react with an alcohol. See Wang, U.S. Pat. No. 5,869,693 and CP-A 2,195,346 and Kuang et al CP-A-2,346,149.

One-step method polymerization was carried out in m-cresol for the synthesis of the acid-containing host polyimide III from 6FDA and DABA monomers. The reaction proceeded according to Scheme 1, given above.

EXAMPLE 11
Acid-Containing Polyimide (III)

To a solution of 3,5-diaminobenzoic acid (DABA) (0.3043 g, 2.000 mmol) in m-cresol (15 mL) was added 6FDA (0.8885 g, 2.000 mmol). The mixture was stirred firstly at 60° C. for 1 hr, and then at 200° C. overnight. Water produced during reaction was removed through a distillation receiver. After cooling to room temperature, the viscous solution was poured slowly into a stirring methanol (500 mL). The precipitated polymer was collected by filtration, washed thoroughly with hot methanol, and dried by heating under vacuum (1.09 g, 97% yield). IR (KBr, cm$^{-1}$): 2614–3509 (O—H of carboxylic acid), 1786 and 1729 (C=O of imide ring), 1601 and 1462 (C—C of phenyl rings).

The inherent viscosity of polyimide m was measured to be 0.76 dLg$^{-1}$ in DMAc at 30±0.1° C., indicating a moderately high molecular weight. Polyimide m can be cast or spin coated into a high-quality, transparent, tough thin film on substrates such as glass and silicon wafer. In addition, this host polymer is also soluble in a number of organic solvents as shown in Table 1.

Although this polymer is particularly preferred, any other polymer with functional groups which react with the functionalized PQDM chromophores can be used, provided that it is suitable for processing into a waveguide structure as known in the art.

D. Grafting PQDM Chromophores onto the Host Polymer

The grafting reaction of PQDM chromophores onto a host polymer with a complementary functional group using a coupling agent leads to the formation of the PQDM-grafted polymers. It is preferred that the chromophore has a hydroxyl group, and that the complementary group (e.g., acid) be present on the polymer, to form a covalent ester bond.

In some cases, it is possible to have the hydroxyl on the polymer and the complementary group on the chromophore. Depending on what the complementary group is, it may be necessary to protect the complementary group with a protector group during the making of the chromophore, and subsequently to remove the protector group before reaction with the polymer. Because it is difficult to de-protect the complementary group without reaction with the zwitterion, this is not preferred.

If desired, some of the complementary functional groups on the polymer can be reacted with non-chromophores, which have the same functional group as the chromophores. Thus some of the sites which could otherwise have been filled with chromophore can be filled with other groups as desired. These other groups can be blocking groups or groups which can react in a subsequent reaction to crosslink the polymer.

Thus, the grafting reaction of hydroxyl-containing PQDM chromophores IIa–e onto a host polymer III using a coupling agent leads to the formation of the PQDM-grafted polymers. The acid group in the polymer reacts with the hydroxyl group in the chromophore to form a covalent ester bond.

If desired, some of the acid groups in the polymer can be reacted with bulky non-chromophore alcohols to add blocking groups as side chains on the polymer, or can be reacted with those having other reactive groups which can be used as crosslinking sites for a further crosslinking reactions.

Generally, the polymers after grafting have the formula:

TABLE 1

Solubility of polymer III in various organic solvents

| m-Cresol | DMSO | DMAc | DMF | THF | Acetone | CHCl$_3$ | CH$_2$Cl$_2$ | AcOH |
|---|---|---|---|---|---|---|---|---|
| + | + | + | + | + | + | − | − | − |

Note: "+": soluble; "−": insoluble. Tests were done with 0.01 g of polymer III in 1.0 mL of solvent.

IV

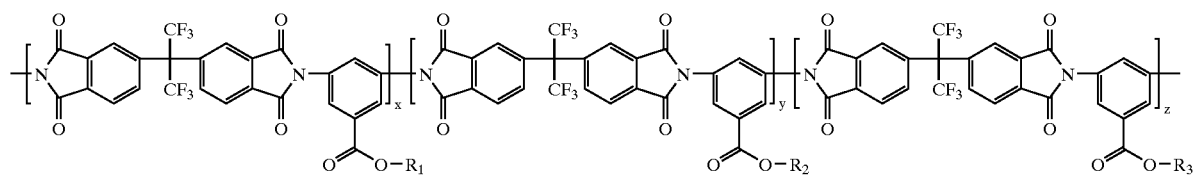

where R1 is a moiety from chromophore IIa–IIe derived by grafting PQDM IIa–e onto polymer III by an esterification graft copolymerization;
$R_2$ is a blocking group
$R_3$ is a crosslinking group
x is at least 1%, and x+y+z=100%, and either or both of y and z can be zero.

Preferably, y and z are zero (in which case all of the grafted side chains are chromophore) or y is zero and x=1–99% with the balance z (in which case some grafted side chains are a crosslinker R3 but none is a blocker R2) or z is zero and x=1–99% (in which case some grafted side chains are a blocker R2 but none is a crosslinker R3).

For example, reaction of PQDM IIb and polyimide III, in the presence of 1-[3-dimethylamino)propyl]-3-ethylcarbo diimide hydrochloride (EDCI) as a coupling agent and 4-dimethylaminopyridine (DMAP) as a base, produced the PQDM-grafted polyimide IV below, where y=z=0. By adding 3,5-di-tert-butylphenol to the reaction, a blocking group is added to the polymer, which is represented by y>0. By adding 5-aminobenzocyclobutenone to the reaction, a crosslinking group is introduced into the resultant polymers, which is represented by z>0. In the resultant polymers, a series of copolymers containing variable amounts of PQDM chromophore, non-chromophore and reactive crosslinker was obtained. In addition to the use of EDCI as a coupling agent, other coupling reactions using different coupling agents can be used for grafting, such as the Mitsunobu reaction using diethyl azobicarboxylate and triphenylphosphine.

The resulting polymers are the following:

moieties, indicating the successful grafting. Due to the strong chromophore-chromophore interaction, the polymers containing only the IIb moiety exhibited poor solubility after isolation from the polymerization solution. When the bulky di-tert-bujtylphenoxy (t-BPO) group was introduced into the polymer backbone, the resulting polymer showed much improved solubility, good film forming property, and high thermal stability. For the purpose of crosslinking, 5-aminobenzocyclobutenone was also introduced into the host polymer system.

The obtained chromophore-containing polymers showed good solubility in polar aprotic solvents such as tetrahydrofuran, N,N-dimethylacetamide (DMAc), N,N-dimethylformamide, and dimethylsulfoxide but not in acetone, although the host polymer m was soluble in acetone. The PQDM polymer solution in DMAc can be used to cast films. The cast thin films are transparently blue, flexible, tough, and can be peeled off from substrate as a free-standing film. No glass transition temperature was detected from these PQDM polymers, due to their rigid backbone structure. The temperature for the initial loss in weight for these polymers is around 150° C. However, the initial loss is likely to be attributed to the loss of trapped solvent in polymer samples, since the PQDM polymers with a strong polarity can act like a host for a polar solvent. The graft polymers are therefore likely to be stable at above 250° C.

Typical reactions to form these graft polymers were as follows:

EXAMPLE 12
Grafting PQDM Chromophore IIb onto Host Polyimide III

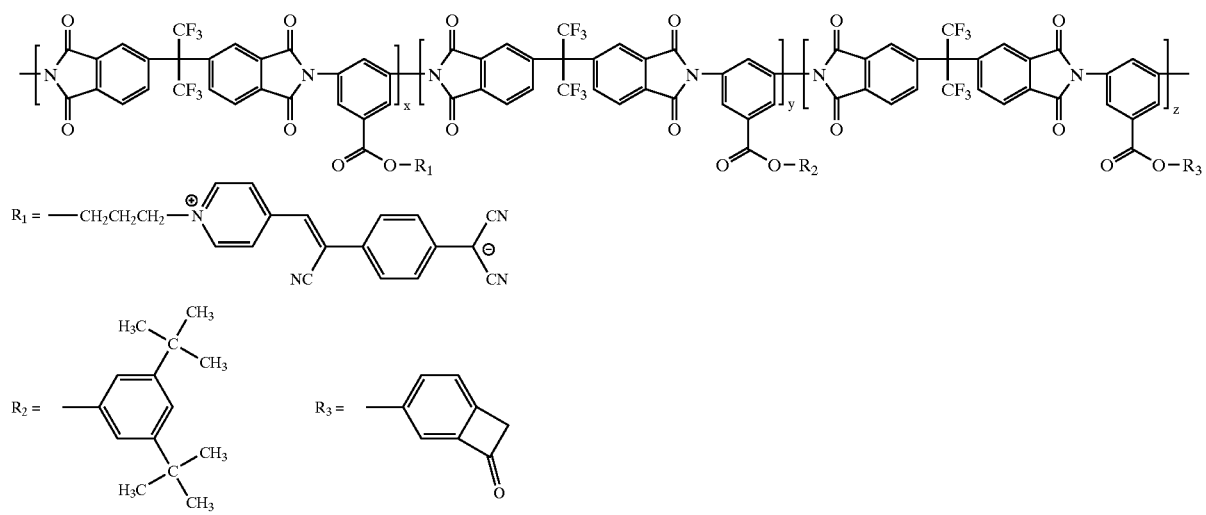

where x is at least 1%, and x+y+z=100%, and either or both of y and z can be zero.

Preferably, y and z are zero (in which case all of the grafted side chains are chromophore) or y is zero and x=1–99% with the balance z (in which case some grafted side chains are a crosslinker R3 but no side chains are blocker R2) or z is zero and x=1–99% (in which case some grafted side chains are blocker R2 but none are crosslinker R3.

All the chromophore-grafted polymers IV were obtained as a blue amorphous solid in nearly quantitative yields. Their IR spectra showed the existence of the cyano and imide To a solution of III (20.0 mg, 35.6 μmol), IIb (10.0 mg, 30.4 μmol), and 4-dimethylaminopyridine (7.0 mg, 57.3 μmol) in N,N-dimethylformamide (0.5 mL) was added 1-[3-dimethylamino)propyl]-3-ethylcarbo diimide hydrochloride (EDCI) (23.0 mg, 120.2 μmol). The solution was stirred at room temperature for 12 hours and then precipitated into methanol. The blue polymer (IV-a) was collected by filtration, extracted with a Soxhlet extractor by methanol overnight, and dried under vacuum (17.0 mg, 64% yield). IR (KBr, cm$^{-1}$). 2176, 2131 ($\upsilon_{C \equiv N}$ of cyano group), 1783, 1727 ($\upsilon_{C=O}$ of imide group).

EXAMPLE 13

Grafting PQDM Chromophore IIb and 3,5-di-tert-butylphenol onto Host Polyimide III.

To a solution of III (0.341 g, 0.609 mmol), IIb (0.150 g, 0.457 mmol), 3,5-di-tert-butylphenol (0.031 g, 0.150 mmol), and 4-dimethylaminopyridine (0.074 g, 0.609 mmol) in anhydrous N,N-dimethylacetamide (4 mL) was added EDCI (0.122 g, 0.638 mmol). The solution was stirred at room temperature for 12 hours and then precipitated into methanol. The blue polymer (IV-e) containing 29 weight percent of the PQDM chromophore (0.46 g, 88% yield) was obtained, after filtration, extracted with a Soxhlet extractor by methanol overnight and dried under vacuum. IR (KBr, cm$^{-1}$): 2176, 2135 ($v_{C \equiv N}$ of cyano group), 1785, 1729 (($v_{C=O}$ of imide group)

EXAMPLE 14

Grafting PQDM Chromophore IIb, 3,5-di-tert-butylphenol (t-BPO) and 5-aminobenzocyclobutenone (BCBO) onto Host Polyimide III To a solution of III (0.090 g, 0.160 mmol), IIb (0.020 g, 0.061 mmol), 5-aminobenzocylcobutenone (0.002 g, 0.016 mmol), 3,5-di-tert-butylphenol (0.013 g, 0.063 mmol) and 4-dimethylaminopyridine (0.020 mg, 0.163 mmol) in anhydrous N,N-dimethylacetamide (3 mL), was added EDCI (0.037 g, 0.193 mmol). The solution was stirred at room temperature for 2 hours and then another portion of IIb (0.020 g, 0.061 mmol) was added. After being stirred at room temperature for 12 hours, the reaction solution was precipitated into methanol. The blue polymer (IV-b) containing 21 weight percent of the PQDM chromophore (0.10 g, 76% yield) was obtained, after filtration, extracted with a Soxhlet extractor by methanol overnight and dried under vacuum. IR (KBr, cm$^{-1}$): 2177, 2131 ($v_{C \equiv N}$ of cyano group), 1783, 1727 (($v_{C=O}$ of imide group).

Characterization of polymers formed by Examples 12, 13 14 and other similar runs were as follows:

TABLE 2

Characterizations of chromophore-grafted polymers IV.

| PQDM Polymer | PQDM IIb Content (x, mol %)[a] | PQDM IIb Content (wt. %)[b] | t-BPO Content (y, mol %)[a] | BCBO Content (z, mol. %)[a] | $T_d$ (° C.)[c] |
|---|---|---|---|---|---|
| IV-a | 100 | Not measured | 0 | 0 | 256 |
| IV-b | 50 | 21 | 40 | 10 | 252 |
| IV-c | 50 | Not measured | 50 | 0 | 248 |
| IV-d | 50 | 22 | 50 | 0 | 250 |
| IV-e | 75 | 29 | 25 | 0 | 240 |

[a]The calculated mol % in feed.
[b]The actual weight percent of IIb incorporated in the polymer was determined by UV-Vis absorption calibration method.
[c]The onset temperature for 5% weight loss as assessed by thermogravimetry in nitrogen with a heating rate of 10° C./min.

The graft polymers in table 2 can be used in electrooptic modulators.

Although the invention has been described with reference to specific embodiments, it will be evident to one skilled in the art that modifications can be made to these embodiments without departing from the spirit and scope of the invention. Accordingly, the invention is not to be limited to the specific embodiments disclosed, but is rather to be construed with respect to the attached claims, including obvious variations therefrom.

What is claimed is:

1. A method of manufacturing a chromophore

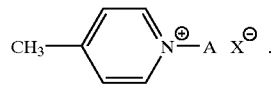

having a functional group selected from the group consisting of –OH; carboxylic acid; acid chloride; alkyl halide selected from the group consisting of —CH$_2$Cl, —CH$_2$Br, and —CH$_2$I; isocyanato; epoxy; and benzocyclobutenone, said method comprising the step of reacting a picolinium halide having the functional group with a lithium tetracyanoquinodimethine adduct.

2. A method as claimed in claim 1 in which the picolinium halide has the formula

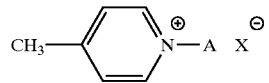

where X Is —Cl or —Br or —I and
where A is a linear or branched alkyl group having 2–20 carbon atoms and said desired functional group, and where the carbon atoms in said alkyl group can have fluorine substituents.

3. A method as claimed in claim 2, in which the desired functional group is —OH.

4. A method as claimed in claim 2, where A is selected from:
   —CH$_2$CH$_2$OH
   —CH$_2$CH$_2$CH$_2$OH
   —CH$_2$CH$_2$CH$_2$CH$_2$CH$_2$CH$_2$OH

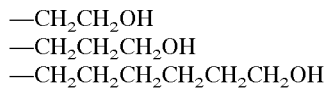

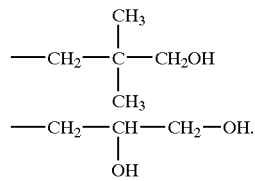

5. A method of making a polymer which has chromophore groups grafted thereon, which comprises:
   (a) providing a polymer with functional groups which react with said desired functional groups of the chromophore of claim 1,
   (b) reacting said chromophore with said polymer to graft said chromophore as side chains onto said polymer to form a graft copolymer.

6. A process as claimed in claim 5, in which said chromophore is formed by the method of claim 4.

7. A process as claimed in claim 5, additionally comprising reacting a tertiary alcohol with said polymer to graft a moiety from said tertiary alcohol onto said polymer as blocking groups.

8. A chromophore having the formula:

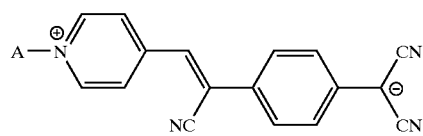

where A has at least one hydroxyl group connected to a linear or branched C$_2$–C$_{20}$ alkyl group and the alkyl group can have fluorine substituents.

9. A chromophore as claimed in claim 8 wherein A has at least one hydroxyl group connected to a linear or branched C$_2$–C$_6$ alkyl group.

10. A chromophore as claimed in claim 8, in which A Is selected from the group consisting of:

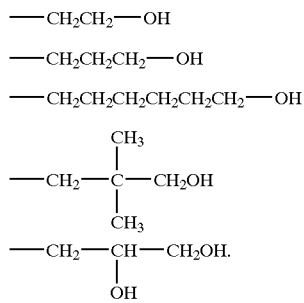

11. A polymer having repealing units selected from the following:

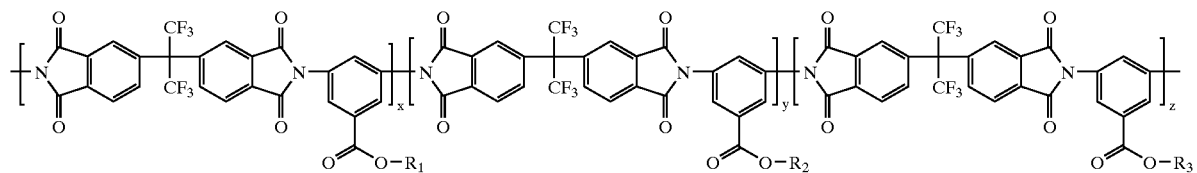

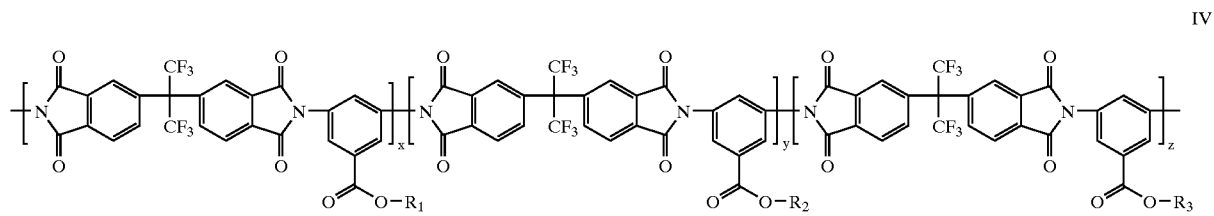

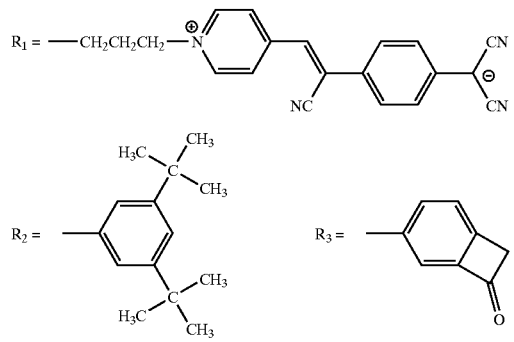

wherein x+y+z=100% of the repeating units, x is at least 1%, and either or both of y and z can be zero R₁ is a chromophore R₂ is a moiety which is not a crosslinker or a chromophore R₃ is a crosslinker.

12. A polymers as claimed in claim 11, in which R₁ is the moiety which remains from the chromophore of claim 8 when it is grafted by esterification graft polymerization onto a polymer having complementary groups.

13. A polymer as claimed in claim 11, in which R₁ is the moiety which remains from the chromophore of claim 10 when it is grafted by esterification graft polymerization onto a polymer having carboxyl groups.

14. A polymer as claimed in claim 13 in which R₂ is the moiety which remains when 3,5-di-tert-butylphenol is graft polymerized by esterification onto a polymer having carboxyl groups.

15. A polymer as claimed in claim 13 in which R₃ is the moiety which remains when 5-aminobenzocyclobutenone is graft polymerized onto a polymer having carboxyl groups.

16. The polymer:

IV

IV wherein x+y+z=100% of the repeating units, x is at least 1%, and either or both of y and z can be zero.

17. A method as claimed in claim 1 in which the desired functional group is —OH.

18. A method as claimed in claim 1, comprising the additional step of protecting said desired functional group with a protector group while reacting said picolinium halide with said lithium tetracyanoquinodimethine adduct.

19. The polymer as claimed in claim 16, in which y=0.

20. The polymer as claimed in claim 16, in which z=0.

* * * * *